(12) United States Patent
Ouellet et al.

(10) Patent No.: US 9,714,910 B2
(45) Date of Patent: Jul. 25, 2017

(54) LIQUID METAL CLEANLINESS ANALYZER

(71) Applicant: ABB Inc., Québec (CA)

(72) Inventors: Réal Ouellet, Québec (CA); Jacques Marcotte, Québec (CA); Patrick Couture, Québec (CA); Sylvio Laplante, Québec (CA); Bruno Simard, Quebéc (CA)

(73) Assignee: ABB Inc. (CA)

( * ) Notice: Subject to any disclaimer, the term of this patent is extended or adjusted under 35 U.S.C. 154(b) by 28 days.

(21) Appl. No.: 14/434,117

(22) PCT Filed: Oct. 10, 2013

(86) PCT No.: PCT/CA2013/000860
§ 371 (c)(1),
(2) Date: Apr. 8, 2015

(87) PCT Pub. No.: WO2014/059517
PCT Pub. Date: Apr. 24, 2014

(65) Prior Publication Data
US 2015/0253267 A1    Sep. 10, 2015

Related U.S. Application Data

(60) Provisional application No. 61/713,703, filed on Oct. 15, 2012.

(51) Int. Cl.
*G01R 27/08*    (2006.01)
*G01N 27/00*    (2006.01)
(Continued)

(52) U.S. Cl.
CPC ............ *G01N 27/00* (2013.01); *G01N 15/12* (2013.01); *G01N 33/206* (2013.01); *G01R 23/02* (2013.01);
(Continued)

(58) Field of Classification Search
CPC ........ G01N 27/00; G01N 15/02; G01N 15/12; G01N 33/206; G06Q 10/06313; G06Q 10/0637; G01R 23/02
(Continued)

(56) References Cited

U.S. PATENT DOCUMENTS

| 4,600,880 A | 7/1986 | Doutre et al. |
| 6,426,615 B1 | 7/2002 | Mehta |
| 2001/0035747 A1* | 11/2001 | Li .................. G01N 33/206 324/71.4 |

OTHER PUBLICATIONS

Notification of First Office Action for China Application No. 2013800588604, dated Apr. 18, 2016, 9 pages.
(Continued)

*Primary Examiner* — Farhana Hoque
(74) *Attorney, Agent, or Firm* — Taft Stettinius & Hollister

(57) ABSTRACT

An apparatus to detect and measure suspended particles in a molten metal where the suspended particles have an associated noise frequency range has in addition to the electrically non-conductive barrier for immersion in the molten-metal, a device to move the molten metal through an orifice in the barrier and electrodes, a time varying excitation source that generates an AC current at a predetermined range of excitation frequency that is out of the predominant noise frequency range to generate an AC signal that is representative of the measure of the suspended particles. A detector detects and quantifies from the measurement AC signal the suspended particles. The detector can be a synchronous detector.

16 Claims, 14 Drawing Sheets

(51) Int. Cl.
*G06Q 10/06* (2012.01)
*G01R 23/02* (2006.01)
*G01N 15/12* (2006.01)
*G01N 33/20* (2006.01)
*G01N 15/02* (2006.01)

(52) U.S. Cl.
CPC ... *G06Q 10/0637* (2013.01); *G06Q 10/06313* (2013.01); *G01N 15/02* (2013.01)

(58) Field of Classification Search
USPC .................................. 324/71.1, 76.39, 693
See application file for complete search history.

(56) References Cited

OTHER PUBLICATIONS

Notification of Second Office Action for China Application No. 2013800588604; dated Dec. 21, 2016, 16 pages.
International Search Report for PCT International Application Serial No. PCT/CA2013/000860, completed Nov. 18, 2013, 2 pages.
International Preliminary Report on Patentability for PCT International Application Serial No. PCT/CA2013/000860, completed Apr. 21, 2015, 5 pages.
Jagtiani, Ashish V., Carletta, Joan and Zhe, Jiang, An Impedimetric Approach for Accurate Particle Sizing Using a Microfluidic Coulter Counter, Mar. 24, 2011, 10 pages.
Payton Steve, Brandt, Milan and Grandfield, John, The Use of Electromagnetic Fields for the Detection of Inclusions in Aluminum, Oct. 8, 2009, 10 pages.
Supplementary European Search Report, for EP13846869, completed May 17, 2018, 10 pages.

* cited by examiner

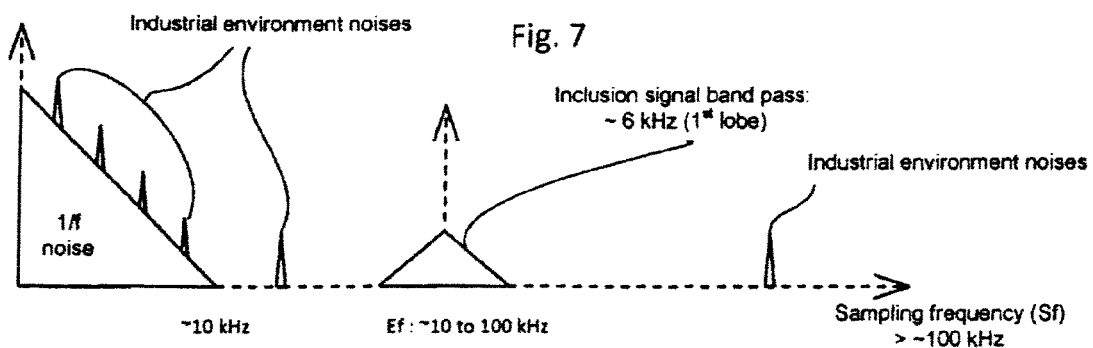

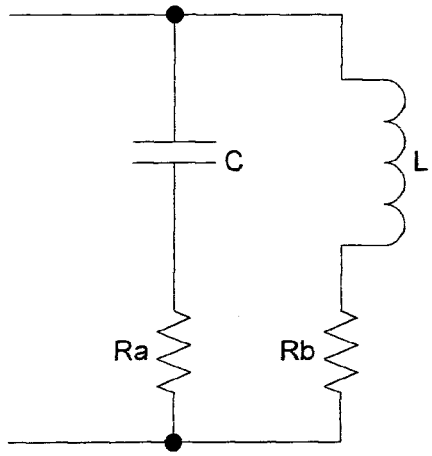
Figure 8a Resonant Tank Circuit AC Source
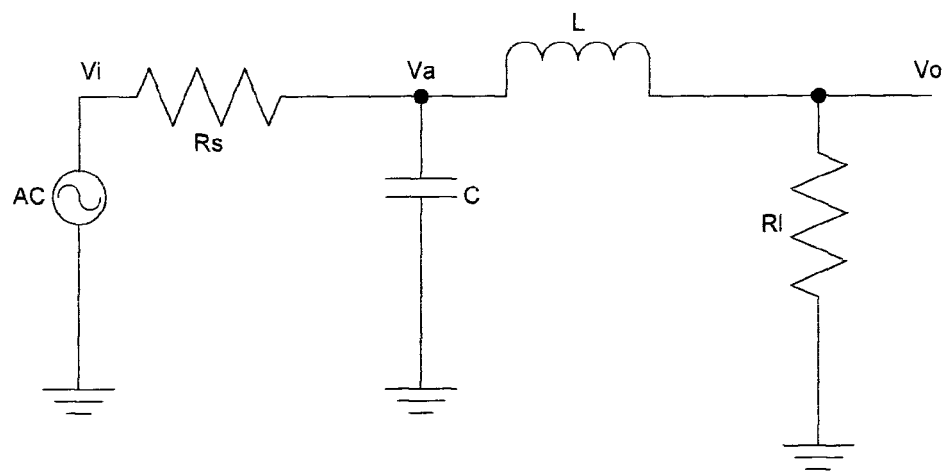
Figure 8b Low Pass Impedance Match AC Source
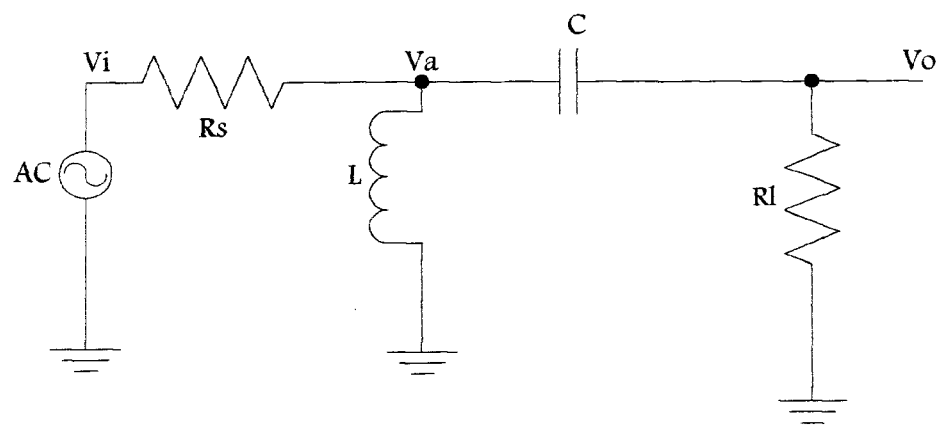
Figure 8c High Pass Impedance Match AC Source

LIQUID METAL CLEANLINESS ANALYZER

FIELD OF THE INVENTION

This invention relates to analyzers that detect suspended particulates in molten metals such as aluminum, gallium, lead, zinc, steel, iron etc. These particulates, also called inclusions are solid, liquid or gaseous particles that have a low electrical conductivity compare to the molten metals.

DESCRIPTION OF THE PRIOR ART

Molten metals, particularly molten aluminum and steel, are frequently contaminated to some extent by entrained inclusions that give rise to a variety of shortcomings or defects in the resulting finished products. Such inclusions can arise from a number of sources, for example, in aluminum through the entrainment of surface oxide films, from the formation of insoluble impurities such as coarse or clustered boride particles, or fine or coarse carbides and nitrides, from the oxidation of alloying elements such as magnesium, and from the erosion of the refractory linings of vessels used to hold or transport the liquid metal.

Problems that are caused by the presence of inclusions include the tearing of the metal during mechanical working operations, the presence of pin-holes and streaks in foils, surface defects and blisters in sheet, and increased rates of breakage during production of wire. These problems are becoming more acute as customers demand thinner, lighter products and better surface appearance, and as the proportion of recycled metal that is used in the production of some sheet metal products rises, with attendant increases in inclusion formation during remelting.

There are liquid metal cleanliness analyzers ("LiMCAs") such as ABB's LiMCA II and LiMCA CM that provide a relatively rapid detection and measurement of the concentration and size distribution of suspended particulates in molten metal. These analyzers both use the same measurement principle, however the LiMCA II uses batteries to accumulate the energy for the direct current used in the measurement and the LiMCA CM uses ultra-capacitors to accumulate the energy for that current. The analyzers can be employed during a processing operation on the molten metal. U.S. Pat. No. 4,600,880 ("the '880 Patent") describes one embodiment for a LiMCA.

SUMMARY OF THE INVENTION

Apparatus for separately detecting and measuring suspended particles in a molten metal where the measuring of the suspended particles has an associated predominant noise frequency range, the apparatus having:

an electrically non-conductive barrier having opposed sides and having an orifice of predetermined hydrodynamic diameter, the barrier being suitable for immersion in a molten metal with the orifice below a surface of the metal;

a device for moving molten metal through the orifice in a direction from one side of the barrier to the other;

electrodes, suitable for immersion in the molten metal, positioned on opposite sides of the barrier for establishing a current path in the molten metal passing through the orifice; and a time varying excitation source for generating an AC current at a predetermined range of excitation frequency which is out of predominant noise's frequency range, the time varying excitation source connectable to the electrodes when the barrier and the electrodes are immersed in the molten metal to use the AC current to measure the suspended particles and generate an AC signal representative of the measurement of the suspended particles.

Apparatus for separately detecting and measuring suspended particles in a molten metal where the measuring of the suspended particles has a predominant noise frequency range and the apparatus has:

an electrically non-conductive barrier having opposed sides and having an orifice of predetermined hydrodynamic diameter with the barrier being suitable for immersion in a molten metal with the orifice below a surface of the metal;

a device for moving molten metal through the orifice in a direction from one side of the barrier to the other;

electrodes, suitable for immersion in the molten metal, positioned on opposite sides of the barrier for establishing a current path in the molten metal passing through the orifice;

a time varying excitation source for generating an AC current at a predetermined range of excitation frequency which is higher than the predominant noise frequency range, the time varying excitation source connectable to the electrodes when the barrier and the electrodes are immersed in the molten metal to use the AC current to measure the suspended particles, wherein the measurement is an AC signal having the excitation source predetermined frequency range; and a detector to detect and quantify from the measurement AC signal the suspended particles in the molten metal.

A system for use in an apparatus that is for separately detecting and measuring suspended particles in a molten metal. The measuring of the suspended particles having a predominant noise frequency range. The apparatus has an electrically non-conductive barrier having an orifice. The barrier is suitable for immersion in a molten metal with the orifice below a surface of the metal. The apparatus also has electrodes that are suitable for immersion in the molten metal. The electrodes are positioned on both sides of the barrier for establishing a current path in the molten metal passing through the orifice.

The system has a time varying excitation source for generating an AC current at a predetermined range of excitation frequency which is out of predominant noise frequency range. The time varying excitation source is for connection to the electrodes so that when the barrier and the electrodes are immersed in the molten metal the AC current can be used to measure the suspended particles. The measurement is an AC signal that has the excitation source predetermined frequency range. The system has a detector that is connected to the source and is for connection to the apparatus to detect and quantify from the measurement AC signal the suspended particles in the molten metal.

DESCRIPTION OF THE DRAWING

FIG. 7 shows the excitation frequency, the inclusion and noise spectral density.

FIG. 8a shows an embodiment for the resonant tank circuit used in the apparatus described herein.

FIG. 8b shows a low pass impedance match circuit as one of the excitation source.

FIG. 8c shows a high pass impedance match circuit as one of the excitation source.

DETAILED DESCRIPTION

Figure 1:
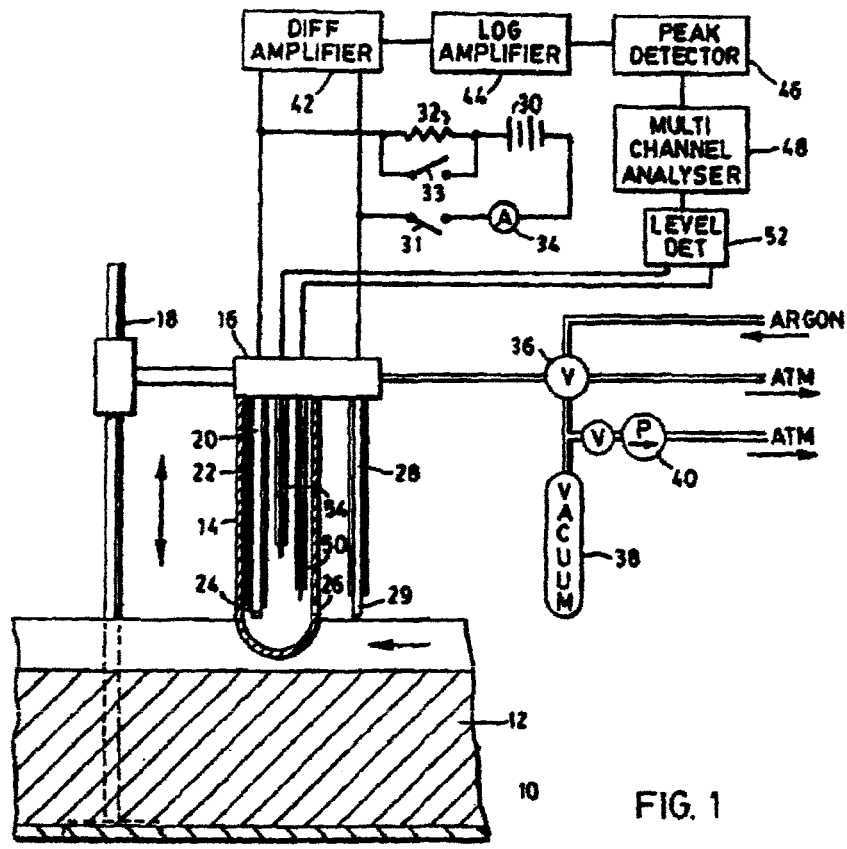
FIG. 1 shows a schematic representation of a prior art liquid metal cleanliness analyzer.
Figure 2:
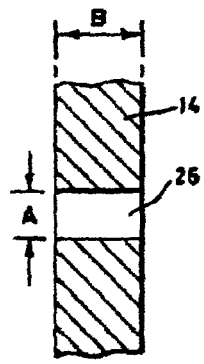
FIG. 2-4 show cross-sections through a sample-receiving vessel of the analyzer of FIG. 1 and show preferred forms of the flow aperture.
Figure 3:
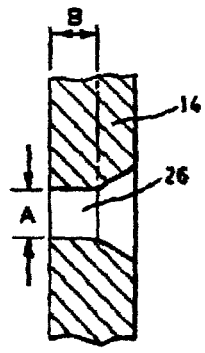
Figure 4:
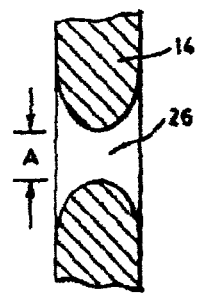

FIGS. 1-4 herein are identical to FIGS. 1-4 of the '880 Patent. As is described in the '880 Patent, a sample-receiving container or vessel 14 (see FIG. 1) is dipped into the flowing stream 12 of molted metal that is to be analyzed. Container 14 has as is shown in FIGS. 1-4, an orifice 26 in the order of 300 um to obtain in vessel 14 a sample of the molted metal when a vacuum is created inside vessel 14. The technique for creating the vacuum is described in the '880 Patent.

The vessel 14 is removably mounted by any suitable means in an end cap 16. The end cap 16 is mounted by a standard 18 for vertical up and down movement, so that the vessel 14 can be dipped at will into the flowing stream 12 and withdrawn therefrom. The end cap 16 has four electrodes 20, 28, 50 and 54 protruding downwardly therefrom. Electrodes 20, 50 and 54 are inside the container 14 and electrode 28 is outside of the container.

The LiMCA inclusions measurement is based on Ohms law, namely that current I through a conductor between two points is directly proportional to the potential difference V across the two points and inversely proportional to the resistance R between them.

The first of three electrodes inside container 14 is a current-carrying electrode 20 consisting of a metal rod the upper part of which is encased in an insulating material 22, so that only the exposed lower tip 24 immediately adjacent to a passage 26 in the container wall is in electrical contact with molten metal that enters the container. A similar current-carrying electrode 28 is mounted by the end cap so as to extend outside the container parallel to the first electrode 20 with its bare lower tip also immediately adjacent to the passage 26.

In the LiMCA of FIG. 1, the resultant current path between the electrodes 20 and 28 and through the passage 26 is supplied with a current normally about 60 A from a battery 30 via a ballast resistor 32 that can be shunted when required by a switch 33, with one of the leads in the path including a switch 31 and an ammeter 34. The short circuiting of resistor 32 allows a current in the range of 120 to 600 A to be applied to a newly formed passage 26 for a specific minimum period of time, at least 1 to 5 seconds, to precondition the passage.

Figure 5:
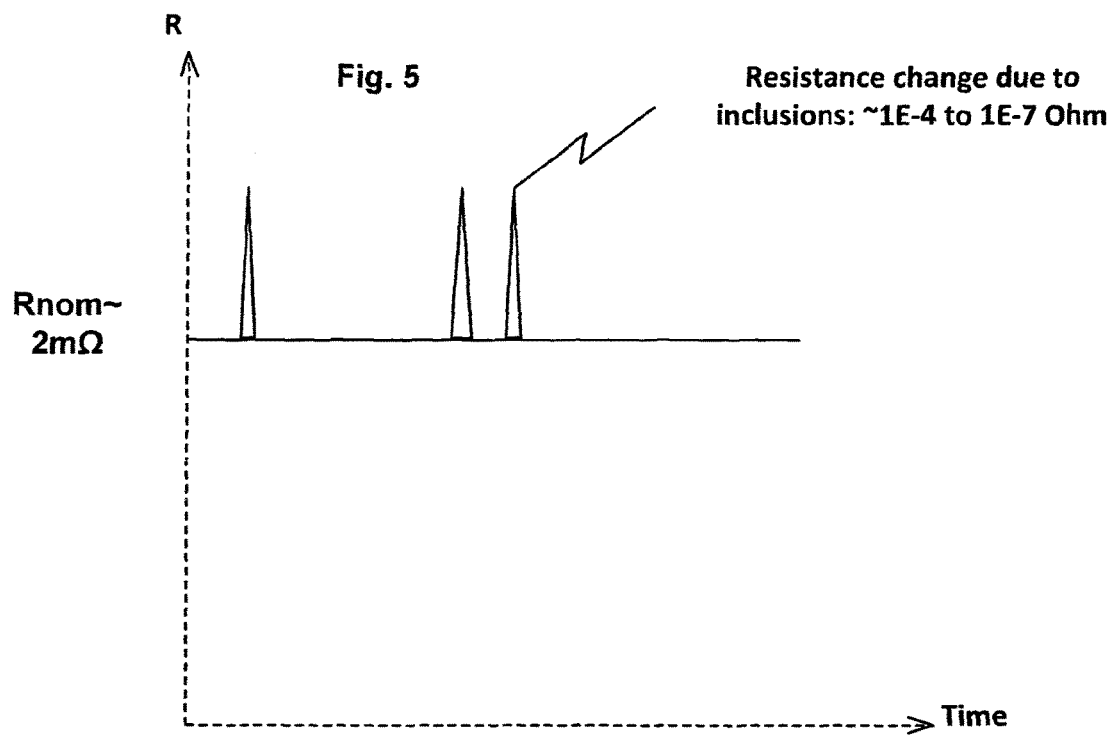
FIG. 5 shows the changes in resistivity when aluminum includes inclusions.

The nominal resistance of a LiMCA, that is, the resistance with no inclusions, is about 2 mΩ. FIG. 5 shows the resistivity changes when aluminum includes inclusions. The changes are in the order of $~10^{-4}$ to $10^{-7} \Omega$ corresponding to inclusion sizes from about 20 to 300 μm. Applying Ohms law to a LiMCA with a normal current of about 60 A, the measured voltage variation is then between $~10^{-3}$ to $10^{-6}$ V.

While FIG. 1 shows a battery 30 as the source of the non-periodic or direct current, as described in patent '880, it is well known to use ultra-capacitance for that source. Either of such sources isolates the generated DC source signal from the noise generated in the plant environment in which the LiMCA is used for the inclusions measurement but they are massive weighing from about 60 kg to 100 kg which substantially reduces the portability of the prior art LiMCA and increases its complexity and maintenance requirements as the batteries will have to be replaced. Noise influencing the LimCA measurement include but are not limited to: pink noise and coupled industrial environment noise. As is well known, pink noise or 1/f noise (sometimes also called flicker noise) is a signal or process with a frequency spectrum such that the power spectral density (energy or power per Hz) is inversely proportional to the frequency. Noise from the industrial environment can be coupled in several ways and can come from many sources, such as: power line, motors, electromagnetic fields. FIG. 7 shows typical noise influencing the LiMCA measurement.

The prior art LiMCA also uses an AC coupling to read the resistivity variations due to the inclusions compared to the nominal probe aperture resistivity.

As is described in more detail below, the apparatus described herein combines a periodic excitation source with detection methods to perform the quantification of the inclusions in various liquid metals. This combination of a periodic excitation source and detection method is used in the detection of the entrained inclusions in molten metals such as aluminum, gallium, zinc, lead, steel, iron etc. The excitation sources include all periodic based generators such as: high current amplifiers for direct electric sensing zone drive, indirect drive via transformers, indirect drive via tuned impedance transformation networks and circuits such as "L, T, n, SP", tank circuits (LC parallel) resonators.

Figure 6:
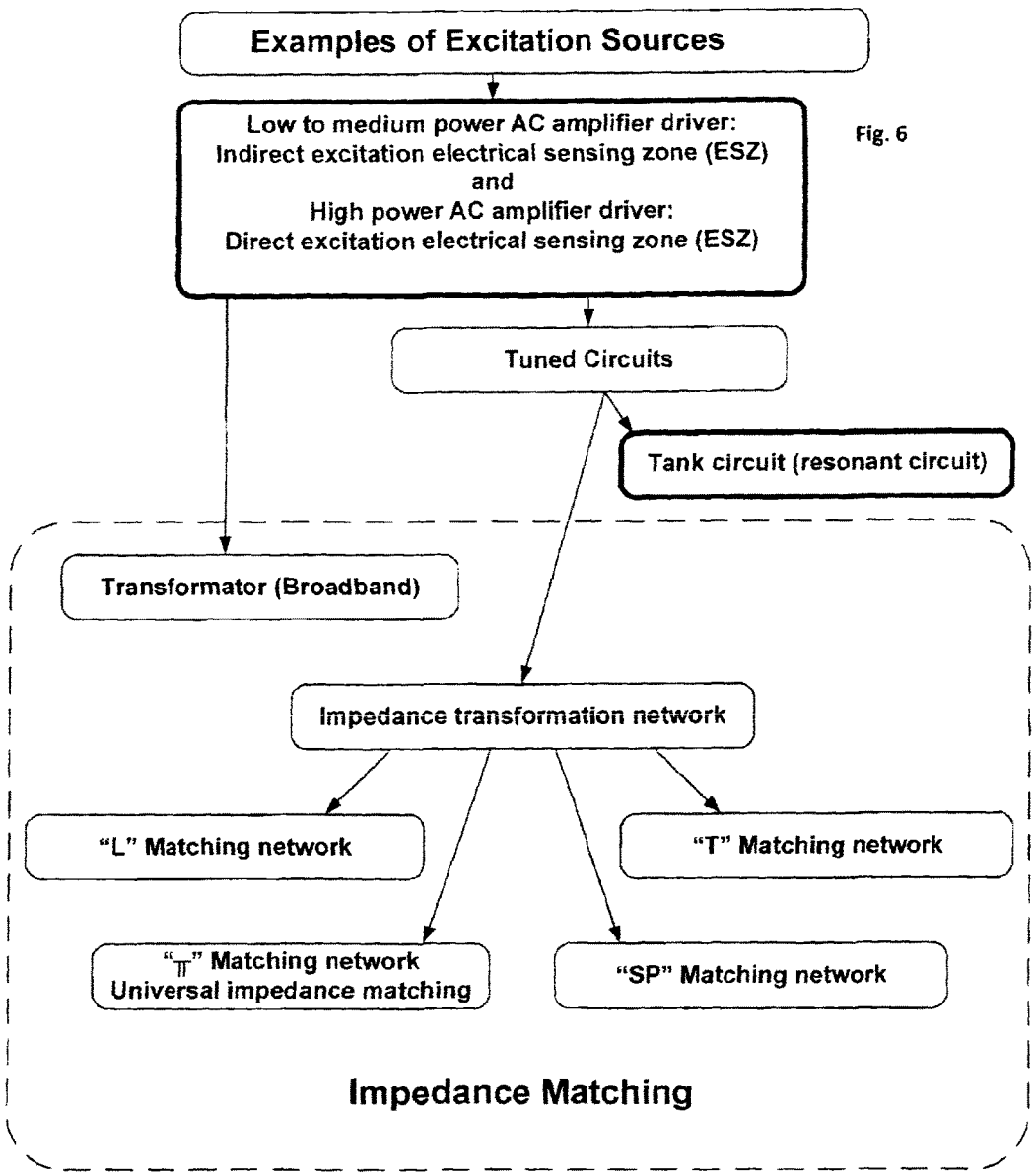
FIG. 6 shows examples of excitation sources for use in the LiMCA described herein.

The detection methods include analog demodulation techniques such as: envelop detector, product detector (synchronous detection, analog or digital lock-in) and digital demodulation techniques such as: digital down converter Examples of the excitation sources for use in the apparatus described herein are shown in the chart attached as FIG. 6. The two major categories of excitation sources are:

Low to medium power (<50 W) AC amplifier driver: indirect excitation electrical sensing zone; and High power 50 W) AC amplifier driver: direct excitation electrical sensing zone.

As is shown in FIG. 6, these categories each have either direct impedance matching through a broadband transformer or a tuned circuit that has impedance matching through an impedance transformation network that can be one of either the "L, T, n, SP" impedance matching network or a resonant circuit.

The use of demodulation techniques to measure very small variations of resistivity helps to immunize the apparatus against those industrial environments that are electromagnetically noisy, for example, those environments that have noise from electromagnetic casting. The use of periodic excitation combined with demodulation techniques greatly reduces the effect of pink noise or 1/f noise at a frequency below 1 kHz, since the signal is than out of the predominant noise's spectral region. Noise as used herein includes pink noise, electromagnetic casting noise and electromagnetic noise arising from other sources in the environment in which the LiMCA described herein is used to detect and measure suspended particles in a molten metal.

Eliminating the batteries and power supply needed to operate the prior art DC excitation version of the LiMCA substantially reduces the overall size and weight of the analyzer and the use of the impedance adaptation and tuned resonating circuits described below allows the efficient generation of high currents in the order of 60 A while greatly reducing the average power dissipated by the circuit.

The apparatus described herein uses a resonant tank circuit to generate the current in the order of 60 A with a frequency of between about 10 kHz to 100 kHz. FIG. 8a shows an embodiment for such a circuit. As is shown in FIG. 8a, the circuit has the series combination of a capacitor C and resistor Ra in parallel with the series combination of an inductor L and a resistor Rb.

As is shown in the chart of FIG. 6, the excitation source may also either be a low pass impedance match circuit one example of which is shown in FIG. 8b or a high pass impedance match circuit one example of which is shown in FIG. 8c. Both circuits have an AC source that provides a voltage Vi. In both circuits, a resistor Rs is connected between the source and a first junction that has a voltage Va. In the low pass circuit of FIG. 8b, an inductor L connects the first junction to a circuit junction at which appears the output voltage Vo. In the high pass circuit of FIG. 8c, a capacitor C connects the first junction to a circuit junction at which appears the output voltage Vo. In the low pass circuit a capacitor C connects the first junction to ground whereas in the high pass circuit an inductor L connects that junction to ground. In both circuits, the second junction is connected to ground through resistor R1.

Figure 9A:
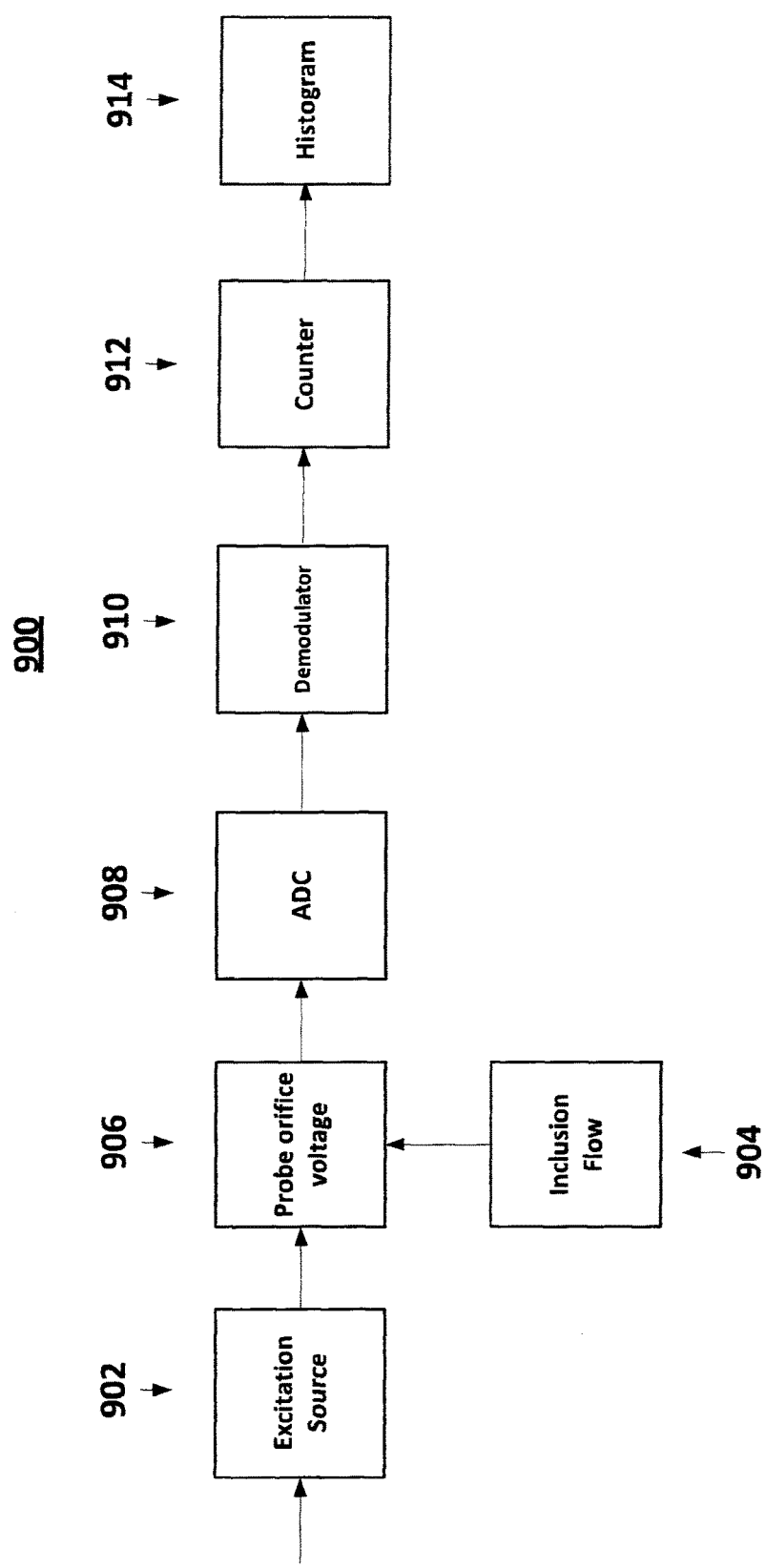
FIGS. 9a and 9b show examples of embodiment of the detector that are used in the LiMCA measurement.
Figure 9B:
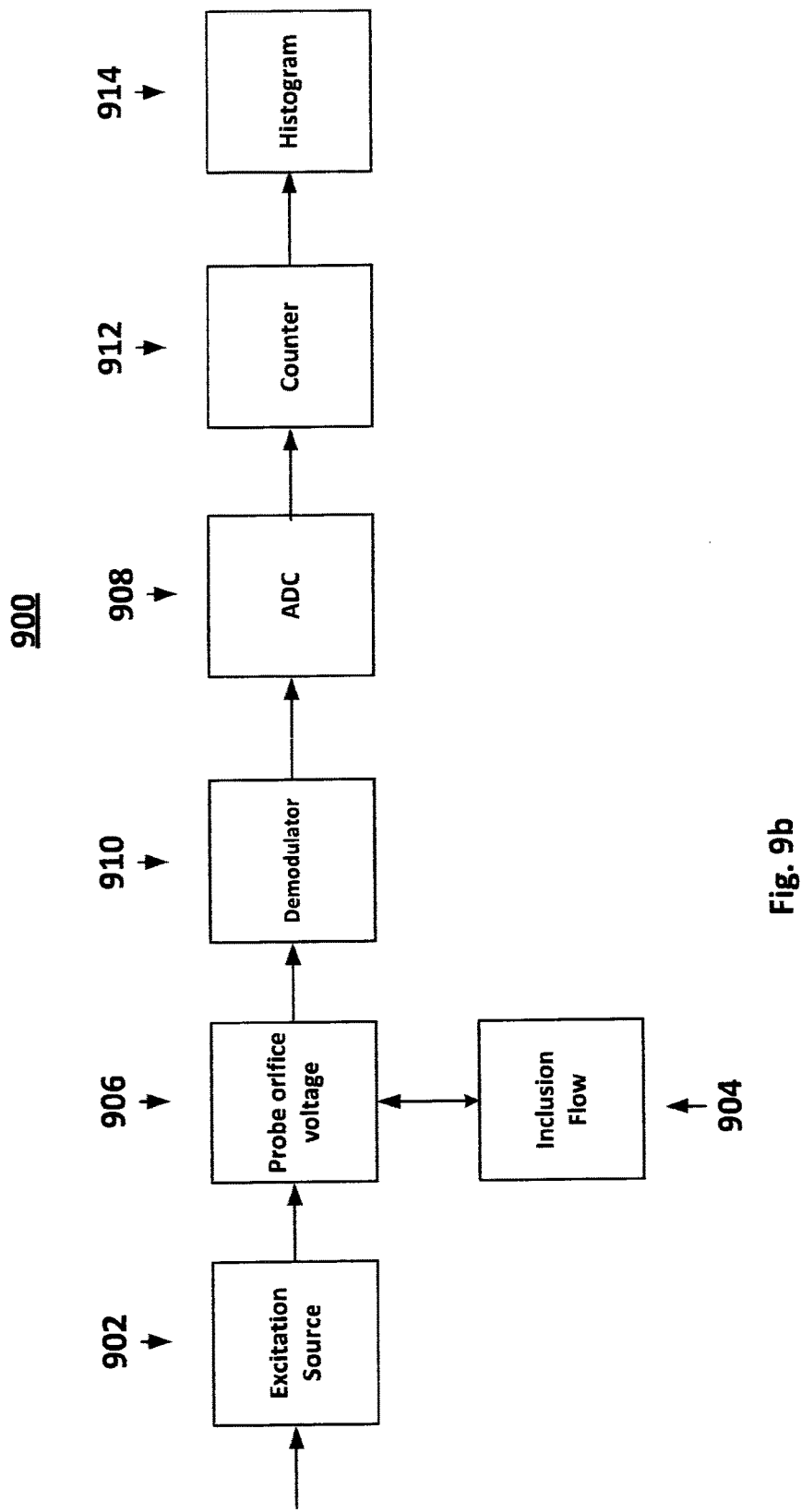

FIG. 9a and FIG. 9b show embodiments of a detector 900 that can be used in the apparatus measurement. The apparatus uses a time varying current source such as any periodic wave as the excitation source 902. The measurement between the electrodes gives a change of resistivity when an inclusion 904 passes through the probe orifice. The change of resistivity translates to a change in voltage 906. In FIG. 9a, the voltage is digitalized using an analog to digital converter (ADC) 908. The digitalized signal is then demodulated by demodulator 910 to retrieve low frequency signal generate by inclusions. In FIG. 9b, the demodulation is performed first by demodulator 910 and then the voltage is digitalized using an analog to digital converter (ADC) 908. Appropriate analog or digital filtering is performed before and after digitalization or demodulation.

The number of inclusions as a function of time is then quantified by counter 912 and shown on a histogram 916. In quantifying the inclusions, counter 912 uses the known non-linear relationship between the height of the signal for each detected inclusion and the size of the inclusion, that is, the suspend particle. The particles that have a size that falls within a predetermined range of inclusion size are grouped together. The histogram 914 shows the number of particles in each group.

Figure 10:
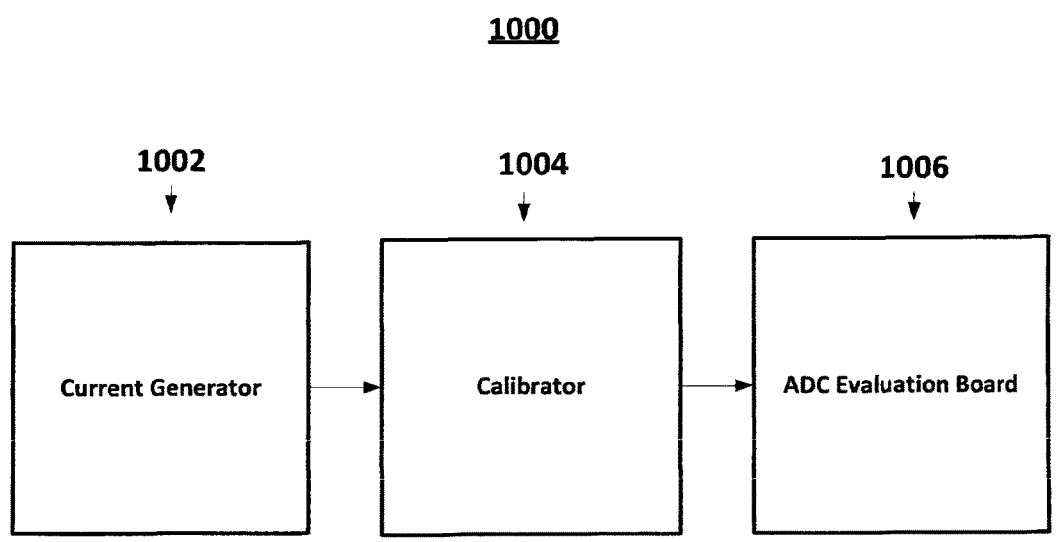
FIG. 10 shows a block diagram of an experimental setup for the apparatus described herein.

Referring now to FIG. 10, there is shown a block diagram of an experimental setup 1000 for the apparatus described herein. Setup 1000 has an AC current source generator 1002, one embodiment for which is shown in the block diagram of FIG. 11.

Figure 11:
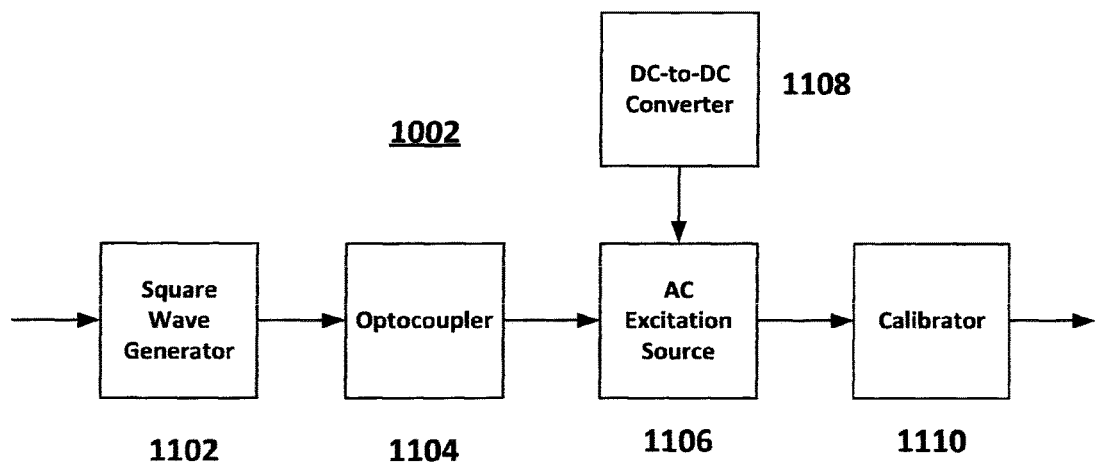
FIG. 11 shows one embodiment for the AC current source generator described herein.

Referring now to FIG. 11, the AC current source generator 1002 has a square wave generator 1102 the output of which is connected to optocoupler 1104. Generator 1002 also has an AC excitation source 1106 having inputs from optocoupler 1104 and DC to DC converter 1108. A Micrel MIC4102 half bridge MOSFET driver can be used to embody source 1106. The output of source 1106 is connected to calibrator 1110.

The experimental setup 1000 of FIG. 10 has a calibrator 1004. Calibrator 1110 of FIG. 11 is identical to calibrator 1004 to simulate various sizes of the inclusions so that setup 1000 does not have to be used on a live process.

Experimental setup 1000 also has an ADC evaluation board 1006. The output of the calibrator 1110 of FIG. 11 is connected to the input of ADC 908 in FIGS. 9a and 9b. Thus the calibrator replaces the functions of the inclusion flow 904 and probe orifice voltage 906 in FIGS. 9a and 9b.

Figure 12:
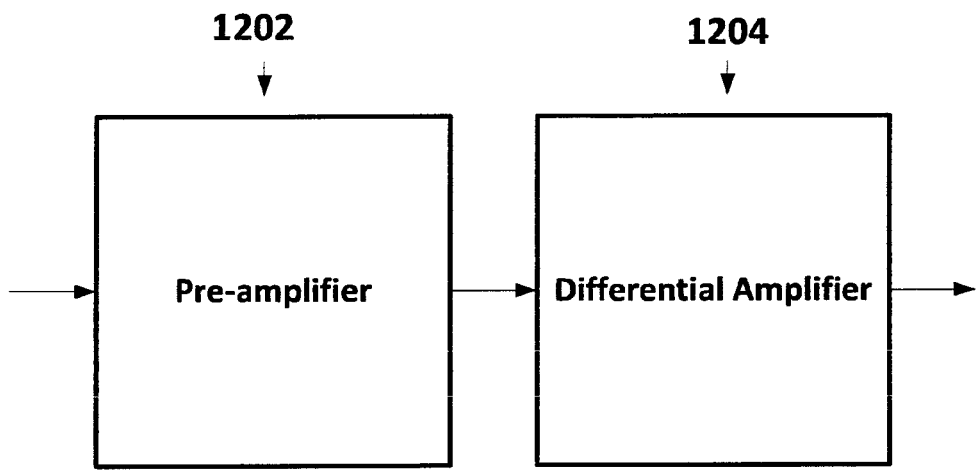
FIG. 12 shows one embodiment for the added amplification in the ADC evaluation board shown in FIG. 10.

The input to board 1006 has an added ultra-low noise amplification front end. One embodiment for the added amplification is shown in FIG. 12 as amplifier 1200. The amplifier is the combination of a pre-amplifier 1202 having an input from calibrator 1004 and a differential amplifier 1204 that can be embodied using a Texas Instruments THS4503 wideband low distortion fully differential amplifier. The output of differential amplifier 1204 is the input to the analog to digital converter. The differential amplifier 1204 allows the use of most of the ADC's dynamic range.

Figure 13:
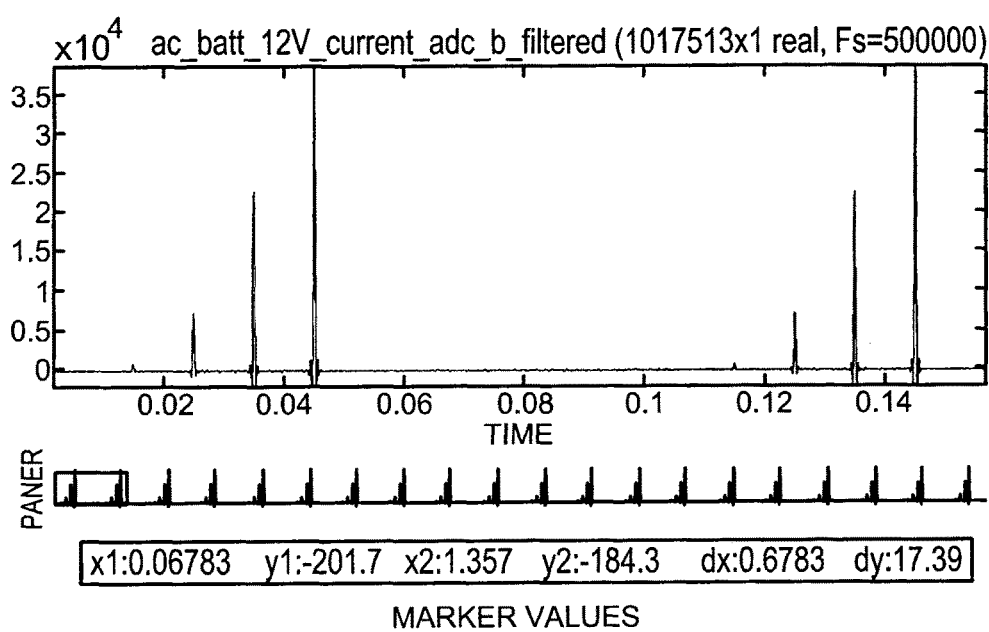
FIG. 13 shows the results of inclusions measurement in the apparatus described herein for an AC source connected to a 12 V battery.
Figure 14:
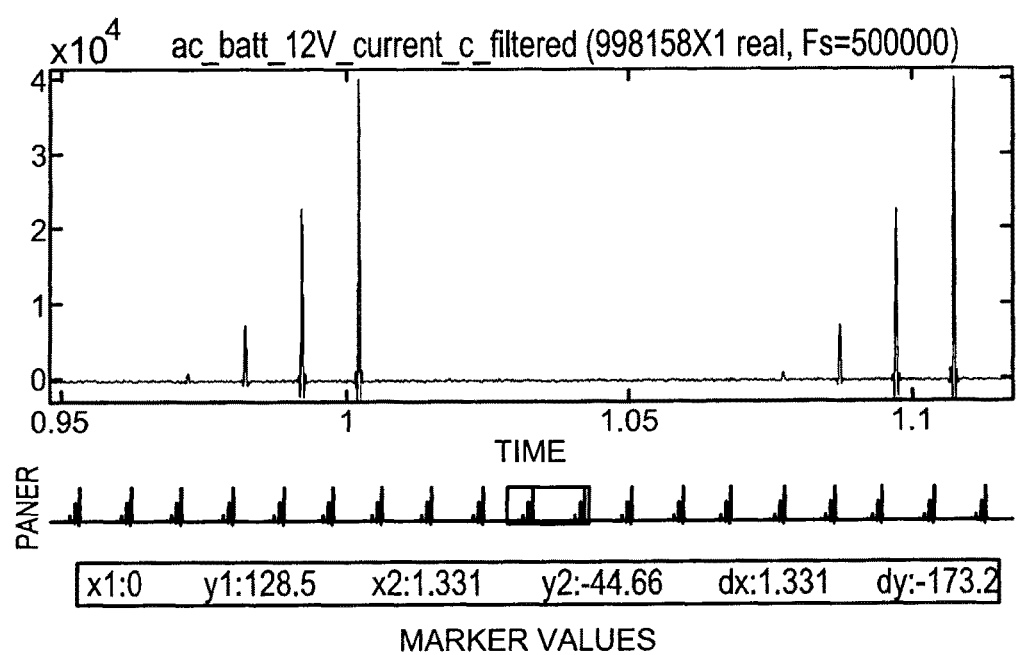
FIG. 14 shows the results of inclusions measurement in the apparatus described herein for an AC source and analog to digital converter connected to a 12 V battery.

Referring now to FIGS. 13 and 14, there is shown the results acquired using setup 1000. The smallest inclusions of the calibrator 1004, which are 20 microns, can be measured with a signal to noise ratio (SNR) of up to 25:1. The other inclusions of the calibrator 1004 which are larger in size can be measured with a SNR better than 25:1. FIG. 13 shows the results for an AC source connected to a 12 V battery and FIG. 14 shows the results for the AC source and ADC connected to a 12 V battery. Therefore the results in FIGS. 13 and 14 show that the apparatus described herein will give good results as compared to the prior art LiMCA's even when a 12 V battery is used as the source of power for the AC current generator.

Figure 15:
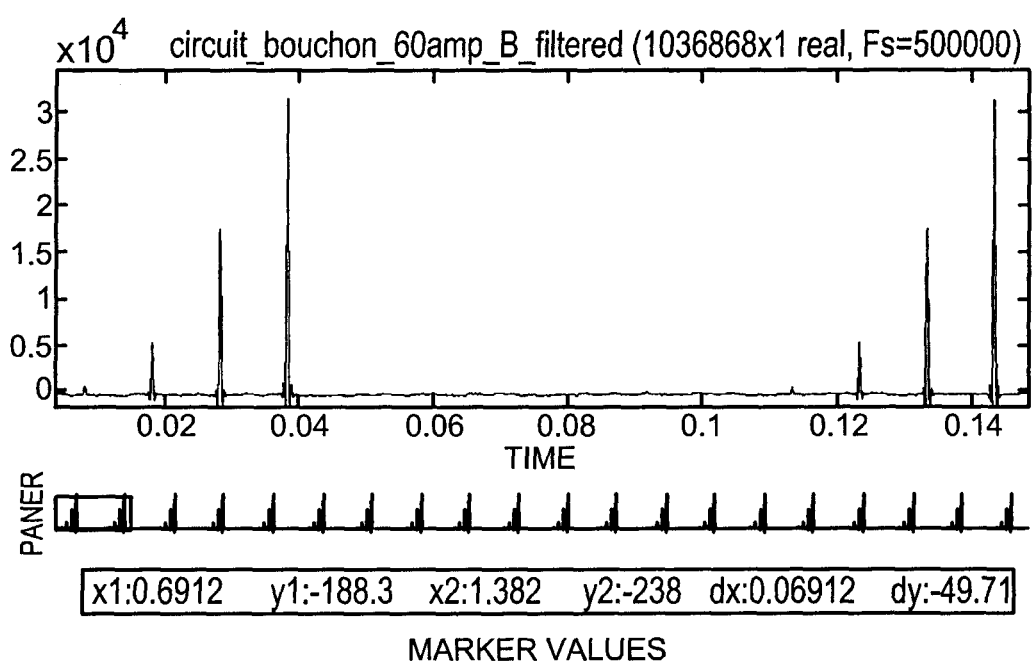
FIG. 15 shows the result of measuring the four simulated inclusions when the resonant circuit is fed from a 120 V AC source.

Referring now to FIG. 15, there is shown the result of measuring the four simulated inclusions when the resonant circuit is fed from a 120 V AC source. As FIG. 15 shows when compared to FIGS. 13 and 14, the results when the resonant circuit is fed from the 120 V AC source are similar to the results of using an AC source connected to a 12 V battery or an AC source and ADC connected to a 12 V battery.

Figure 16:
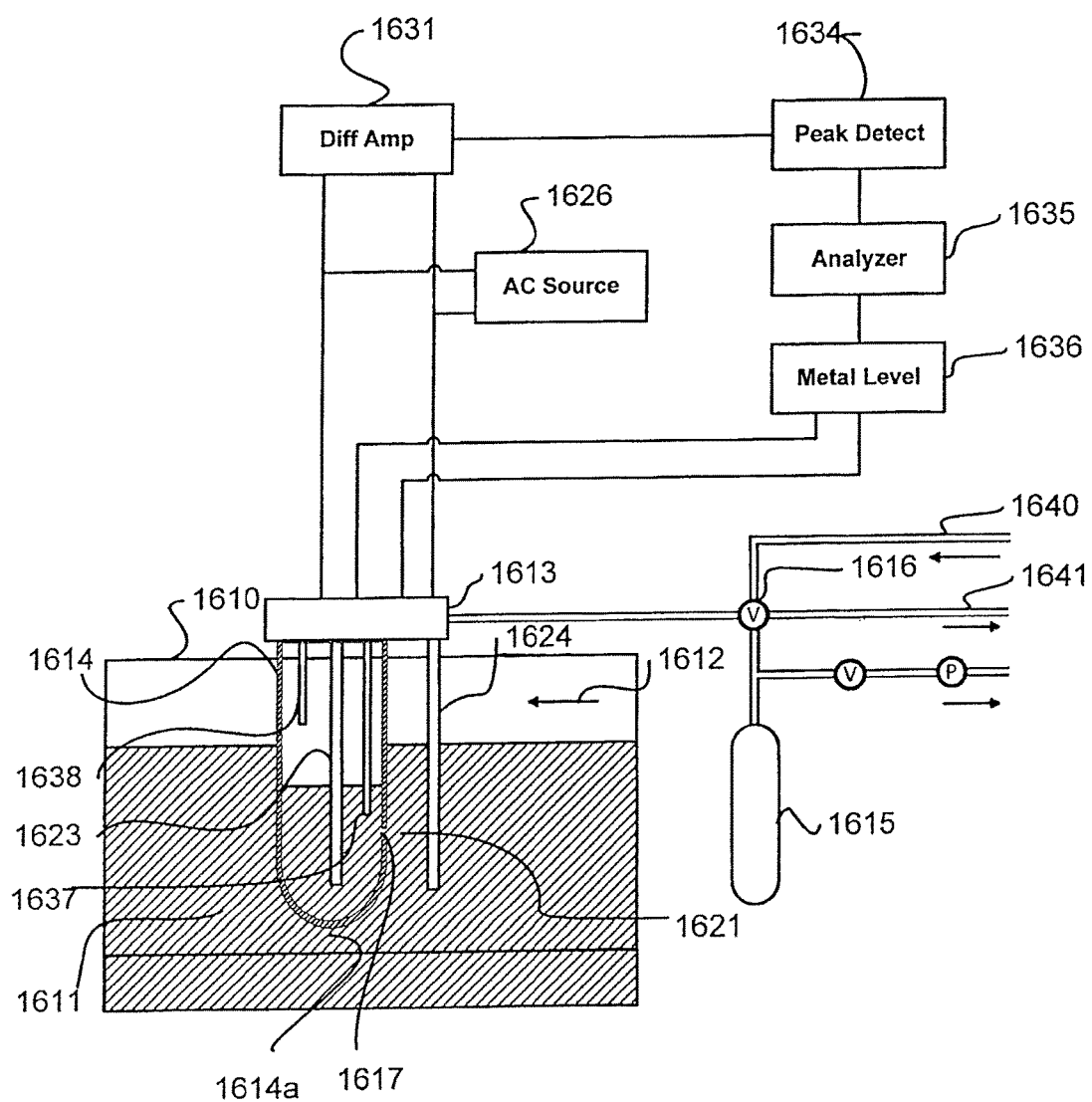
FIG. 16 shows a schematic representation for the LiMCA described herein.

Referring now to FIG. 16, there is shown diagram of the LiMCA described herein in use to measure inclusions. A closed sample receiving container or vessel 1614 having an outer wall 1614a is dipped in the flowing stream 1611 of molten metal. The arrow 1612 shows the direction of flow of stream 1611 in delivery trough 1610. Container 1614 has an orifice 1617 that has a passage 1621 to obtain a sample of the molten metal when a vacuum is created inside vessel 1614.

The vessel 1614 is suitably mounted in a retaining head 1613. The mechanism that provides up and down movement of the vessel 1614 is not shown in FIG. 16. The retaining head 1613 has four electrodes 1623, 1624, 1637 and 1638 protruding downwardly from the head. Electrodes 1623, 1637 and 1638 are inside vessel 1614 and electrode 1624 is outside of the vessel. Electrodes 1623 and 1624 are the current carrying electrodes and their lower tips are adjacent orifice 1617 when a measurement is made.

The current is supplied by AC current source 1626 which can be embodied by any one of the excitation sources described herein. The two electrodes 1623 and 1624 are connected to a differential amplifier 1631 embodied as described herein. The output of the amplifier 1631 is connected to peak detector 1634 embodied as described herein and then to an analyzer/recorder 1635 and a metal level detector 1636 to head 1613.

The head 1613 also provides a fluid connection from the interior of the container 1614 to a three-way valve 1616, which permits the interior to be connected alternatively to a source of reduced pressure, or to a source of a suitable shielding inert gas, such as argon, or to the atmosphere. The reduced pressure source consists of a vacuum source 1615 which is exhausted as required in between measures through valve by a pump. The pump is shut off while the measures are underway, so that any electrical noise produced by its electric motor does not hinder electrical signal processing, and so that any pulsations in flow of the evacuating gas are not transmitted to the entering molten metal.

The interior of the container 1614 is flushed before use with argon gas supplied by gas line 1640 to avoid as much as possible contamination of the metal by air. The container 1614 is then lowered into the stream, and the valve 1616 is operated to connect the container interior to the reduced pressure reservoir, whereupon the molten metal is drawn smoothly and rapidly through the passage orifice 1617. As soon as enough metal has entered the container to touch the tip of the electrode 1623 a current path is established between the two electrodes 1623 and 1624 and through the orifice.

It should be appreciated that the time varying excitation source and detector described herein can be used in an apparatus that has the barrier and electrodes that are described herein for detecting and measuring suspended particles in a molten metal as a replacement for the current source and associated detection circuitry now used in that apparatus.

It is to be understood that the description of the foregoing exemplary embodiment(s) is (are) intended to be only illustrative, rather than exhaustive, of the present invention. Those of ordinary skill will be able to make certain additions, deletions, and/or modifications to the embodiment(s) of the disclosed subject matter without departing from the spirit of the invention or its scope, as defined by the appended claims.

What is claimed is:

1. Apparatus for separately detecting and measuring suspended particles in a molten metal, said measuring of said suspended particles having an associated predominant noise frequency range, said apparatus comprising:
    an electrically non-conductive barrier having opposed sides and having an orifice of predetermined hydrodynamic diameter, said barrier being suitable for immersion in a molten metal with said orifice below a surface of the metal;
    a device for moving molten metal through the orifice in a direction from one side of the barrier to the other;
    electrodes, suitable for immersion in said molten metal, positioned on opposite sides of said barrier for establishing a current path in the molten metal passing through said orifice; and
    a time varying excitation source for generating an AC current at a predetermined range of excitation frequency which is out of said predominant noise frequency range, said time varying excitation source connectable to said electrodes when said barrier and said electrodes are immersed in said molten metal to use said AC current to measure said suspended particles and generate an AC signal representative of said measurement of said suspended particles.

2. The apparatus of claim 1 wherein said predetermined excitation source frequency range of said AC current is between about 10 kHz to 100 kHz.

3. The apparatus of claim 2 wherein said predetermined excitation frequency range of said AC current is between about 10 kHz to less than 100 kHz.

4. The apparatus of claim 1 wherein said time varying excitation source is a resonant tank circuit.

5. The apparatus of claim 1 wherein said time varying excitation source can either be a low pass impedance match circuit or a high pass impedance match circuit.

6. The apparatus of claim 1 wherein said AC signal representative of said measurement of said suspended particles is measured and said apparatus further comprises a demodulator to recover the signal.

7. The apparatus of claim 1 wherein said AC signal representative of said measurement of said suspended particles has said predetermined excitation source frequency range and is measured and said apparatus uses Ohms law to calculate a voltage from said AC signal.

8. The apparatus of claim 7 further comprising an analog to digital converter to digitize said voltage and a filter to filter said digitized voltage to provide a signal that can be used to quantify the suspended particles as a function of time in said molten metal.

9. Apparatus for separately detecting and measuring suspended particles in a molten metal, said measuring of said suspended particles having a predominant noise frequency range, said apparatus comprising:
    an electrically non-conductive barrier having opposed sides and having an orifice of predetermined hydrodynamic diameter, said barrier being suitable for immersion in a molten metal with said orifice below a surface of the metal;
    a device for moving molten metal through the orifice in a direction from one side of the barrier to the other;
    electrodes, suitable for immersion in said molten metal, positioned on opposite sides of said barrier for establishing a current path in the molten metal passing through said orifice;
    a time varying excitation source for generating an AC current at a predetermined range of excitation frequency which is higher than said predominant noise frequency range, said time varying excitation source connectable to said electrodes when said barrier and said electrodes are immersed in said molten metal to use said AC current to measure said suspended particles, wherein said measurement is an AC signal having said excitation source predetermined frequency range; and
    a detector to detect and quantify from said measurement AC signal said suspended particles in said molten metal.

10. The apparatus of claim 9 wherein said detector is a product detector.

11. The apparatus of claim 9 wherein said detector is an envelope detector.

12. The apparatus of claim 9 wherein said detector is a digital demodulation detector.

13. A system for use in an apparatus for separately detecting and measuring suspended particles in a molten metal, said measuring of said suspended particles having a predominant noise frequency range, said apparatus comprising:

an electrically non-conductive barrier having an orifice, said barrier being suitable for immersion in a molten metal with said orifice below a surface of the metal; and electrodes, suitable for immersion in said molten metal, positioned in said barrier for establishing a current path in the molten metal passing through said orifice;

said system comprising:

a time varying excitation source for generating an AC current at a predetermined range of excitation frequency which is out of said predominant noise frequency range, said time varying excitation source for connection to said electrodes so that when said barrier and said electrodes are immersed in said molten metal said AC current can be used to measure said suspended particles, wherein said measurement is an AC signal having said excitation source predetermined frequency range; and a detector connected to said source and for connection to said apparatus to detect and quantify from said measurement AC signal said suspended particles in said molten metal.

14. The system of claim 13 wherein said detector is a product detector.

15. The system of claim 13 wherein said detector is an envelope detector.

16. The system of claim 13 wherein said detector is a digital demodulation detector.

* * * * *